United States Patent

Lavie et al.

[11] Patent Number: 5,824,654
[45] Date of Patent: Oct. 20, 1998

[54] METHOD FOR DELIVERY OF NUCLEIC ACIDS TO CELLS USING HYPERICIN POLYAMINE COMPLEXES

[75] Inventors: Gad Lavie, Rehovot, Israel; Alfred M. Prince, Pound Ridge, N.Y.

[73] Assignees: New York University; New York Blood Center, both of New York, N.Y.

[21] Appl. No.: 300,725

[22] Filed: Sep. 2, 1994

[51] Int. Cl.$^6$ ............... A61K 48/00; C09B 3/40; C12N 5/00
[52] U.S. Cl. ............. 514/44; 435/172.1; 435/172.3; 435/240.1; 530/324; 536/23.1; 552/282; 935/52
[58] Field of Search ............... 514/12, 44, 675, 514/762; 435/172.1, 172.3, 240.1; 530/324; 536/23.1; 552/282; 568/303, 308, 367; 935/52

[56] References Cited

U.S. PATENT DOCUMENTS 5,166,320  11/1992  Wu et al. ............... 530/395

OTHER PUBLICATIONS

A Kabanov et al (1993) Bioconjugate Chem 4: 448–454.
W Stremmel et al (1985) Proc Natl Acad Sci USA 82: 4–8.
X Zhou et al (1991) Biochimica et Biophysica Acta 1065: 8–14.
D Muruelo et al (1988) Proc Natl Acad Sci USA 85: 5230–5240.
N Miller et al (1994) Parasitology Today 10: 92–97.
RA Stull et al (1995) Pharmaceutical Research 12: 465–483.
S Wu–Pong (1994) Pharmaceutical Technology 118: 102–114.
RW Wagner (1994) Nature 372: 333–335.
T Ubbink–Kok et al (1986) Antimicrobial Agents and Chemotherapy 30: 147–151.
KW Culver et al (1994) Trends in Genetics 10: 174–178.
N Miller et al (1995) FASEB J 9: 190–199.
CP Hodgson et al (1995) Exp Opin Ther Patents 5: 459–468.
E Marshall (1995) Science 269: 1050–1055.

Primary Examiner—Bruce R. Campell
Attorney, Agent, or Firm—Darby & Darby

[57] ABSTRACT

The invention provides improved methods for delivery of nucleic acids to cells, which comprise forming ternary complexes between a hydrophobic, membrane-binding anion such as hypericin; a polycation such as polylysine; and a nucleic acid such as DNA; and contacting cells with the tenary complexes. Also provided are pharmaceutical formulations comprising these ternary complexes and a pharmaceutically acceptable carrier or diluent. The methods and compositions find use in mediating DNA uptake into cells, including gene therapy applications.

19 Claims, 5 Drawing Sheets

FIG. 3

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: n/a     ( v i i ) IMMEDIATE SOURCE:
        ( B ) CLONE: seq.id.no.1

( x i ) SEQUENCE DESCRIPTION: SEQ ID NO:1:

CCAGGCTGTT CCGCAGATTG TGCGGCGCCC CTGACT     36

( 2 ) INFORMATION FOR SEQ ID NO:2:

( i ) SEQUENCE CHARACTERISTICS:

(A) LENGTH: 28 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (vi) ORIGINAL SOURCE:
            (A) ORGANISM: Human immunodeficiency virus type 1

(vii) IMMEDIATE SOURCE:
            (B) CLONE: HIV GAG 776-802 ANTISENSE (xi) SEQUENCE DESCRIPTION: SEQ ID NO:2:

CGCTCTCGCA CCCATCTCTC TCCTTCTA                                                           28

METHOD FOR DELIVERY OF NUCLEIC ACIDS TO CELLS USING HYPERICIN POLYAMINE COMPLEXES

FIELD OF THE INVENTION

This invention pertains to improved methods for delivery of nucleic acids to cells, which methods can be applied to gene therapy.

BACKGROUND OF THE INVENTION

Advances in the understanding of the molecular basis of disease have led to the development of methods to treat diseases by introducing foreign DNA into affected cells. The foreign DNA may act by interfering with the expression of deleterious genes, whether they are host genes, or genes of viruses or other invading microorganisms. For example, timely interference with the expression of certain viral early genes by administration of antisense DNA to infected cells in culture can forestall their interaction with cellular tumor suppressor genes; in this manner, oncogenic transformation caused by the virus can be inhibited (Pietenpol et al., 1990, Cell 61:777–785). Another example is the long-term treatment of human immunodeficiency virus-infected cells with antisense oligonucleotides. In this case, the antisense oligonucleotides hybridize to viral mRNA molecules and directly inhibit translation of viral proteins (Lisziewicz et al., 1993, Proc. Natl. Acad. Sci. USA 90:3860–3864). Another approach involves the introduction into a cell of catalytic RNAs ("ribozymes"), which contain autocleavage domains and can selectively hydrolyze and inactivate RNA targets, whether host-derived or foreign (Foster et al, 1987, Cell 49:211–220; Rossi et al., 1991, Pharmacol. Ther., 50:245–254.

Alternatively, the introduced DNA may act positively, by supplying alternative or supplemental genes whose expression counteracts the pathological condition. For example, introduction of the adenosine deaminase gene can overcome immunodeficiency, or introduction of the cystic fibrosis transmembrane receptor (CFTR) gene into cystic fibrosis respiratory epithelial cells improves bronchial mucous fluidity and facilitates mucous removal and alveolar function.

In either case, for effective gene therapy, the active nucleic acid must be efficiently introduced into the target cells in an intact and functional form. One difficulty is that exogenous DNA is often degraded by nucleases before it encounters its target cell. A solution to this problem is to modify the phosphodiester bond between deoxyribose sugar moieties in DNA by e.g. substitution with a methyl phosphonate, phosphoramidate, and most effectively, with a phoshorothioate bond (Agrawal et al., 1989, Proc. Natl. Acad. Sci. USA, 86:7790–7794).

A second problem is that nucleic acids are polyanions at physiological pH, causing them to be repelled from cell surfaces which are predominantly negatively charged. Furthermore, nucleic acids are extremely hydrophilic, making it difficult for them to penetrate the hydrophobic barrier of the cell membrane. Strategies for neutralizing the negative charges on nucleic acids have employed positively charged molecules, particularly polycations such as polylysine, that interact with both the DNA and the cell surface (Stevenson et al., 1989, J. Gen. Virol., 70:2673–2682; Lemaitre et al., 1987, Proc. Natl. Acad. Sci. USA, 84:648–652). The problem of the hydrophobic cell membrane barrier, however, has been less tractable.

The above-described obstacles in delivering nucleic acids to cells are exacerbated when the goal is to administer these agents to a patient for therapeutic purposes. Thus, there is a need in the art for methods and compositions that facilitate the delivery and uptake of DNA into cells, specifically to overcome the hydrophobic barrier.

SUMMARY OF THE INVENTION

It has now been discovered that formation of ternary complexes between DNA, polylysine, and hypericin or hypericin analogues, results in an effective vehicle for DNA uptake into cells. The invention encompasses a method for delivering nucleic acids to cells, comprising the steps of:
(i) contacting
  (a) hypericin or a hypericin analogue, or salts thereof; and
  (b) a polycation such as polylysine to form a binary complex;
(ii) incubating the binary complex with a nucleic acid, such as DNA or RNA, thereby forming a ternary complex between the hypericin or hypericin analogue, the polycation, and the nucleic acid; and
(iii) contacting the cells with the ternary complex mixture.

An alternative embodiment of the present invention provides a method for delivering nucleic acids to cells, comprising the steps of:
(i) contacting
  (a) a hydrophobic, membrane binding anion, or salts thereof; and
  (b) a polycation to form a binary complex;
(ii) incubating the binary complex with the nucleic acid, thereby forming a ternary complex between the anion, the polycation, and the nucleic acid; and
(iii) contacting the cells with the ternary complex.

The invention also encompasses forming a quaternary complex between hypericin or a hypericin analogue, a polycation such as polylysine, a nucleic acid such as DNA or RNA, and low-density lipoprotein, which can be delivered to cells bearing the low-density lipoprotein receptor or receptor-related proteins.

The invention also encompasses pharmaceutical compositions for delivering nucleic acids to cells, comprising complexes between hypericin or hypericin analogues, a polycation such as polylysine, and a nucleic acid such as DNA or RNA, with or without low-density lipoprotein.

DETAILED DESCRIPTION OF THE INVENTION

All patent applications, patents, and literature references cited in this specification are hereby incorporated by reference in their entirety. In case of inconsistencies, the present description, including definitions, will prevail.

Definitions

1. "Nucleic acid" as used herein denotes DNA, both single- and double-stranded, with a sugar backbone of deoxyribose, methylphosphonate, or phosphorothioate; "protein nucleic acid" (PNA), which comprises nucleotides bound to an amino acid backbone; and all forms of RNA, including mRNA and ribozymes.

2. "Antisense" oligonucleotides as used herein denotes oligodeoxyribonucleotides and oligoribonucleotides comprising a nucleotide sequence that is complementary to a known nucleic acid sequence.

The present invention is directed to methods and compositions for delivery of nucleic acids into cells. Specifically, a ternary complex is formed between the nucleic acid, a polycation, and a hydrophobic, membrane-binding anion. The complex serves as an effective delivery vehicle for cellular uptake of the nucleic acid.

Hydrophobic, membrane-binding anions useful in practicing the present invention are shown below.

1) Polycylic aromatic diones of the structure wherein $R_1$ is H, OH, $CH_3$, $(CH_2)_nCH_3$, $COCH_3$, $CO(CH_2)_nCH_3$, $CH(CH_3)_2$, or $COO(CH_2)_nCH_3$, where n=1–20;
$R_2$ is H, OH, $CH_3$, $(CH_2)_nCH_3$, $COCH_3$, $CO(CH_2)_nCH_3$, $CH(CH_3)_2$, or $COO(CH_2)_nCH_3$, where n=1–20;
$R_3$ is H, OH, or $COCH_3$; and
$R_4$ is H, OH, or $COCH_3$.

2) Anthraquinones of the structure wherein $R_1$ is H, OH, $CH_3$, $COCH_3$, $(CH_2)_nCH_3$, or $CO(CH_2)_nCH_3$, where n=1–20;
$R_2$ is H, OH, or $COCH_3$;
$R_3$ is H, OH, or $COCH_3$; and
$R_4$ is H, OH, $COCH_3$, $(CH_2)_nCH_3$, or $CO(CH_2)_nCH_3$, where n=1–20.

3) Emodin anthrone derivatives of the structure wherein $R_1$ is H, OH, $CH_3$, $COCH_3$, $(CH_2)_nCH_3$, or $CO(CH_2)_nCH_3$, where n=1–20;
$R_2$ is H, OH, or $COCH_3$;
$R_3$ is H, OH, or $COCH_3$; and
$R_4$ is H, OH, $COCH_3$, $(CH_2)_nCH_3$, or $CO(CH_2)_nCH_3$, where n=1–20.
A preferred member of the above class of compounds is emodin anthrone in which $R_1$ is $CH_3$, $R_2$ is OH, $R_3$ is OH, and $R_4$ is OH.

4) Cercosporine derivatives of the structure or wherein $R_1$ is H, OH, $CH_3$, $COCH_3$, $(CH_2)_nCH_3$, or $CO(CH_2)_nCH_3$, wherein n=1–20; and
$R_2$ is H, OH, $CH_3$, $COCH_3$, $(CH_2)_nCH_3$, or $CO(CH_2)_nCH_3$, wherein n=1–20; and
5) Fatty acids of the structure $CH_3(CH_2)_nCOOH$, wherein n=1–20.

Hypericin and its analogues are aromatic, polycyclic diones which are lipophilic molecules that exhibit a high affinity for cell membranes of various cell types (Meruelo et al., in *Natural Products as Antiviral Agents,* Chu and Cutler, eds., Plenum Press, New York, 1992, pages 91–119). One basis for this affinity is the ability of these substances to bind phosphatidyl choline, an abundant component of cell membranes (Lavie et al., in *Trends in Medicinal Chemistry* 90: *Proceedings of the XIth International Symposium on Medicinal Chemistry,* 1990, pages 321–327). Hypericin has also been shown to bind low-density lipoprotein (LDL) with an association constant of 0.44 mM and a hypericin:LDL molar ratio of up to 467:1 per 10,000 daltons of LDL particles (Meruelo et al., *op cit.;* Lavie et al., *op cit.*)

Non-limiting examples of hypericin analogues useful in practicing the present invention include pseudohypericin, hypericin-methyl ester, hypericin-propyl ester, hypericin isopropyl ester, hypericin-butyl ester, hypericin-isobutyl ester, hypericin dicarboxylic acid, desmethyl hypericin, and hydroxydesmethyl hypericin. Hypericin and hypericin methyl ester are particularly preferred for use in the present invention because they exhibit high affinity for cell membranes.

Hypericin and its analogues may be used as salts. For example, sodium hypericin and potassium hypericin are useful, since when mixed with polylysine hydrobromide they readily form sodium bromide or potassium bromide, respectively, and the polylysine salt of hypericin. This is easily detected by the color shift of an aqueous dispersion of sodium hypericin (pink) after complexing with polylysine (blue).

Hypericin and several of these analogues are shown in FIG. 1. Hypericin is commercially available from Sigma (St. Louis, Mo.) and Aldrich. Hypericin may be synthesized from emodin by alkaline self-condensation (Spitzner, 1977, *Agnew Chem. Int. Engl. Ed.,* 16:46). An improved method for synthesis of hypericin is provided in Lavie et al., *Trends in Medicinal Chemistry* '90: *Proceedings of the XIth International Symposium on Medicinal Chemistry,* pages 321–327. Hypericin analogues may be synthesized from their respective anthraquinone derivatives of emodin (Rodewald et al., 1977, *Angew Chem. Int. Engl. Ed.,* 16:46–47). Hypericin can also be obtained by extraction and purification from the St. Johnswort Plant (Hypericum) as disclosed in Meruelo et al., 1988, *Proc. Natl. Acad. Sci. USA* 85:5230–5234.

In one embodiment, the present invention encompasses the formation of ternary complexes comprising 1) nucleic acid, 2) a polycation, and 3) a hydrophobic membrane-binding anion such as hypericin or a hypericin analogue. The polycation serves as a positively charged "skeleton" to which the negatively charged nucleic acid and the hypericin both bind (see Example 1 below). Preferably the polycation is polylysine. Polylysine may comprise high- or low-molecular weight forms, the low-molecular weight polymers (i.e. 5000–20,000 daltons) being preferred for applications involving small oligonucleotides, and the high-molecular weight forms (i.e. up to 300,000 daltons) being preferred for other applications. For example, polylysine is commercially available in molecular weights ranging from 7–8,000 daltons and degree of polymerization of 60–80 monomers (Sigma P-6516) to 350,000 daltons and degree of polymerization 1600 monomers (Sigma P-1886). Non-limiting examples of other polycations useful in practicing the present invention include polyarginine (Sigma), polyasparagine (Sigma), polymethyleneamine, polyethyleneamine, polypropyleneamine, polyisopropyleneamine, polybutyleneamine, polyisobutyleneamine, polypentyleneamine and polyisopentyleneamine.

Formation of the above described complexes is independent of the nature and sequence of the nucleic acid employed. Thus, the invention encompasses complexes formed from DNA or RNA. The DNA may be linear or circular, may be single-stranded or double-stranded, and may range in size from about 10 to about 25,000 nucleotides in length. The DNA may comprise antisense oligonucleotides, and may further include nuclease-resistant phosphorothioate, phosphoroamidate, and methylphosphonate derivatives, as well as "protein nucleic acid" (PNA) formed by conjugating bases to an amino acid backbone as described in Nielsen et al., 1991, *Science* 254: 1497. The DNA may be derivatized by linkage of the a-anomer nucleotide, or by formation of a methyl or ethyl phosphotriester or an alkyl phosphoramidate linkage. Alternatively, the DNA may be derivatized in other ways known in the art, including e.g. biotinylation.

In addition, the DNA may comprise a complete gene expression system, when it is desired to supplement the gene expression repertoire of the target cell. In this embodiment, the DNA contains regulatory and structural genes, including constitutive and/or inducible promoter sequences that allow expression of the desired gene. Non-limiting examples of promoters suitable for use in the present invention include the constitutive cytomegalovirus promoter and the steroid-inducible mouse mammary tumor virus promoter. Structural genes include without limitation wild-type tumor suppressor genes, to replace mutated or internally deleted copies of such genes (e.g. p53, retinoblastoma, Wilm's tumor genes); genes such as that encoding CFTR (cystic fibrosis transmembrane regulator); and genes encoding ribozymes.

The RNA may comprise any naturally occurring or synthetic single or double stranded linear or circular RNA, including but not limited to messenger RNA, ribosomal RNA, transfer RNA, ribozymes, or subsequences or derivatives thereof. Ribozymes are particularly useful in practicing the present invention, since they can be designed to cleave the mRNA of a specific gene targeted for inactivation. Ribozymes for use in the present invention are produced by Innovir, Inc. (New York, N.Y.).

In forming the ternary complexes between hypericin, polycation, and nucleic acid, an important consideration is the molar ratio between the components. It is desirable that a small number of the positive charges of the polycation be bound to hypericin, with the majority available to bind to the nucleic acid. Thus, the degree of polymerization of the polycation must be taken into account. For example, when using a polycation comprised of 60–80 monomers, about one to about 8 moles of hypericin are mixed with one mole of polycation. Similarly, for a polycation of 100–1500 monomers, about 4 to about 200 moles of hypericin are used per mole of polycation. For a polycation of 1600–2000 monomers, about one to about 300 moles of hypericin are used per mole polycation, preferably about 50 to about 300 moles. For example, a suitable binary complex between polylysine and hypericin may be prepared by mixing 200 $\mu$l of a 0.2 mg/ml solution of low-molecular weight polylysine (degree of polymerization of 60–80 monomers) with 1.25 $\mu$l of sodium hypericin (2 mg/ml in ethanol) to produce a 1:1 molar complex of hypericin:polylysine. Mixing of 6 $\mu$l of the identical hypericin solution with an equivalent amount of polylysine produces a 4:1 molar complex of hypericin:polylysine.

Once the hypericin:polylysine binary complex is formed, nucleic acids are then added so as to form a molar ratio of nucleic acid to polylysine of between about 0.01 to about 2. For relatively low-molecular mass nucleic acids, a ratio of 0.1–2 is preferred, and an equimolar mixture is most preferred. For high-molecular-mass DNAs, by contrast, it is desirable that hypericin-polycation complexes adhere at multiple sites along the DNA; in these cases, up to a 100-fold molar excess of hypericin-polylysine over DNA may be used. For example, for a DNA consisting of 36 bases (molecular mass=13,000 daltons), 25 μmoles of polylysine are mixed with about 20 μmoles of DNA.

To form the complexes, an aqueous solution of polycation (hydrochloride or hydrobromide) is mixed with an aqueous solution of hypericin (sodium salt or potassium salt), followed by addition of nucleic acid. Alternatively, the polycation, hypericin, and nucleic acid may be mixed substantially simultaneously to form the ternary complex. After formation of the final ternary complexes, the solution is buffered using any acceptable system e.g. 50 mM Tris-HCl, 25 nM $MgCl_2$ pH 7.9, etc.

The final ternary complexes are then introduced into cultured cells by simple mixing of about 1 to about 50 μl of the hypericin-polycation-nucleic acid mixture per 1 ml of culture medium. For in vivo administration, the complexes can be administered in a dose of from about 0.01 to about 10 mg complex per kg body weight. Administration may be by intravenous, intramuscular, or subcutaneous routes, as well as by direct introduction into a specific site e.g. into a tumor. For in vivo administration of complexes comprising low-molecular-mass DNA (i.e. 15–30 bases or base pairs), preferably 10–500 μg/kg body weight are administered. For larger species of DNA e.g. $10^4$ base pairs, 50–1000 μg/kg body weight are administered.

In another embodiment, the ternary complex consisting of nucleic acid, polycation, and hypericin, is supplemented with low-density lipoprotein (LDL) to form quaternary complexes i.e. nucleic acid-polycation-hypericin-LDL. In this case, the strong affinity between LDL and the LDL receptor serves to target the quaternary complex specifically to cells bearing the LDL receptor and LDL-receptor-related proteins (LRPs). Such cells include hepatocytes and neuronal cells (Mahley et al., 1988, *Science* 240:622; Innerarity et al., 1990, *Curr. Opin. Lipidology* 1:87.) LDL for use in the present invention may be obtained from Sigma Chemical Co.

The present invention is applicable to deliver nucleic acids to cells in culture, to create protein "factories" capable of producing large amounts of an exogenous protein. It is also contemplated that the methods and compositions of the present invention can be applied to gene therapy, when it is desired to administer specific nucleic acids that encode a desired gene product to a patient to ameliorate a pathological condition. In this case, complexes comprising the nucleic acid, polycation, and hypericin/hypericin analogue, with or without low-density lipoprotein, can be administered in a pharmaceutically acceptable carrier such as sterile saline or phosphate-buffered saline. Routes of administration include intravenous, intramuscular, subcutaneous, intraarticular, and by inhalation.

In an alternative embodiment, the present invention also encompasses compositions comprising the above-described complexes. In yet another embodiment, the present invention provides pharmaceutical formulations comprising the above-described complexes. The complexes may be prepared as lyophilized powders, or as solutions in pharmaceutically acceptable carriers or diluents such sterile saline or phosphate-buffered saline.

The following examples are intended to further illustrate the invention without limiting it thereof.

EXAMPLE 1

Formation of Complexes between Hypericin, Polylysine, and DNA

Figure 1A:
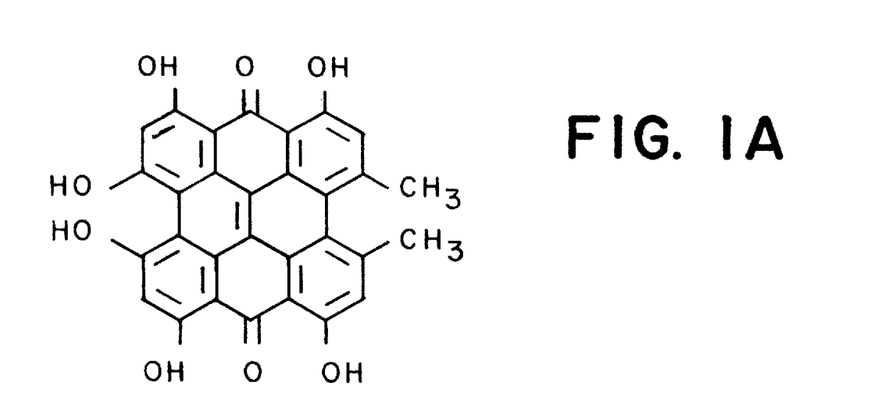
FIG. 1A shows the chemical structure of hypericin.
Figure 1B:
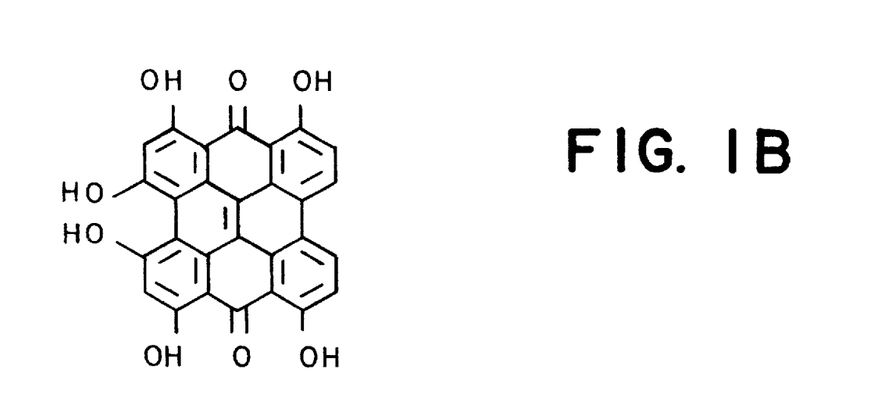
FIG. 1B shows the chemical structure of desmethyl hypericin.
Figure 1C:
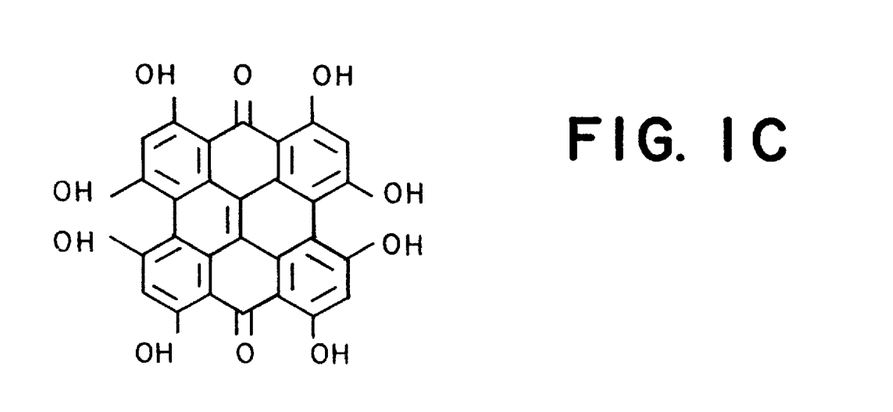
FIG. 1C shows the chemical structure of hydroxydesmethyl hypericin.
Figure 1D:
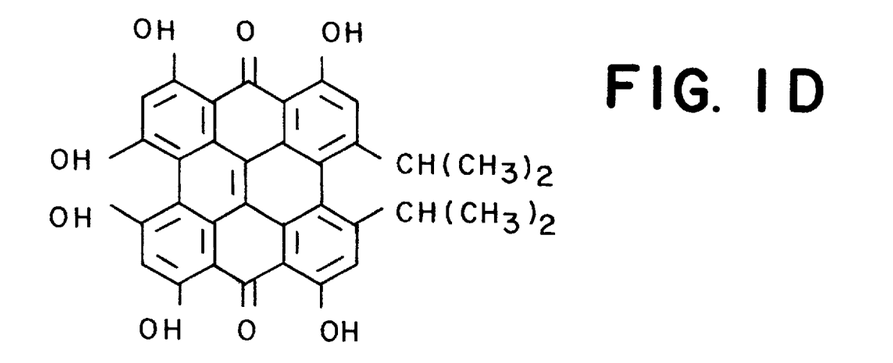
FIG. 1D shows the chemical structure of isopropyl hypericin.
Figure 1E:
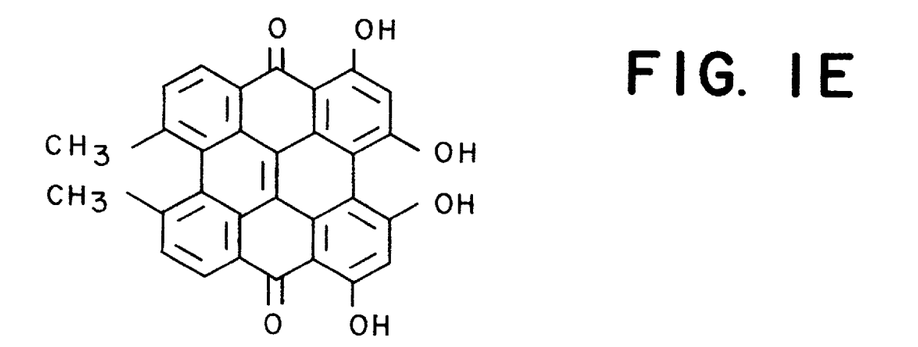
FIG. 1E shows the chemical structure of dibenyzperylene quinone.
Figure 1F:
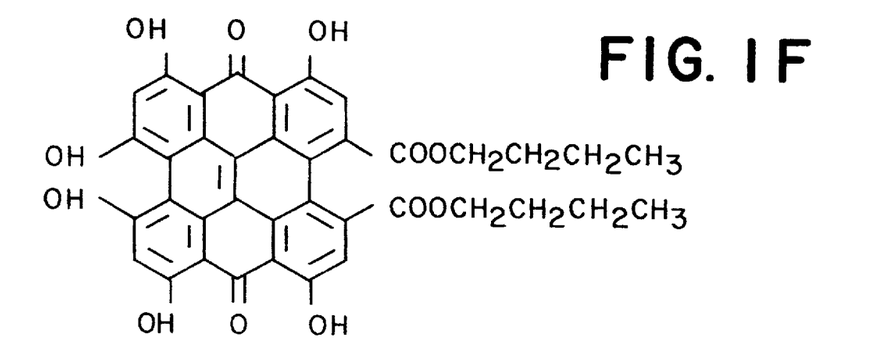
FIG. 1F shows the chemical structure of the butyl ester of hypericic acid.
Figure 2A:
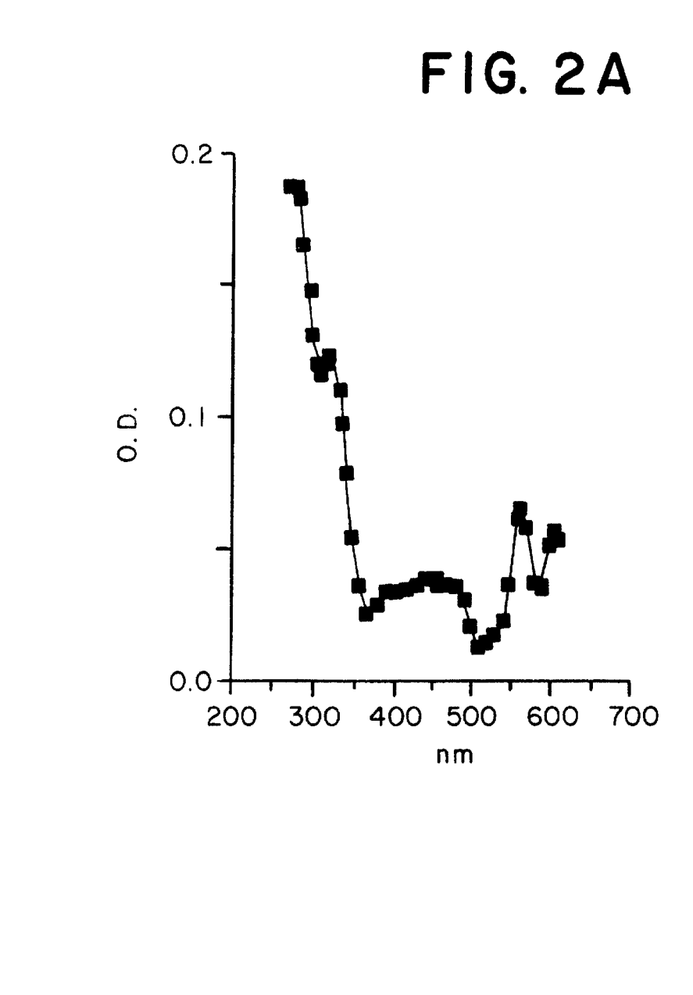
FIG. 2a shows the absorption spectrum of hypericin-polylysine complexes.
Figure 2B:
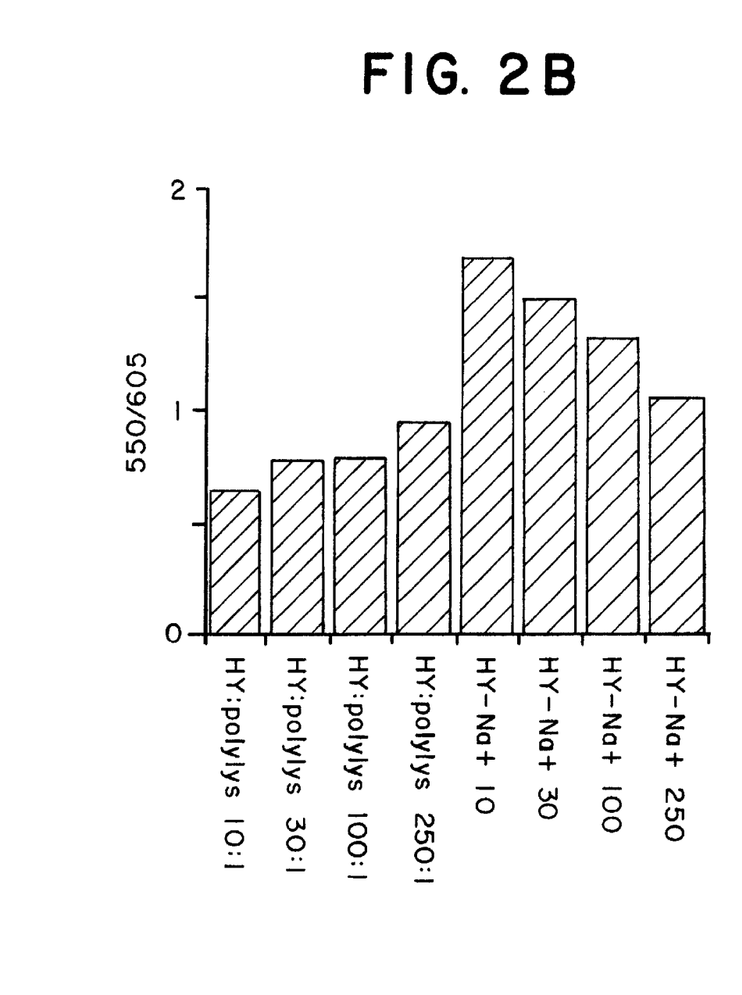
FIG. 2b is a graphic representation of the ratio between the absorption peaks at 550 nm and 605 nm of hypericin (HY-Na) at different molar concentrations, and of hypericin-polylysine complexes at different molar ratios.

A solution of hypericin (2 mg/ml in ethanol) was mixed with an aqueous solution of polylysine hydrobromide (Sigma P-1886, molecular weight=350,000, degree of polymerization=1600). The absorption spectrum of hypericin was red-shifted, with the appearance of an absorption peak at 605 nm (FIG. 2A). The ratios of the absorbance at 550 and 605 nm were compared in solutions containing different molar ratios of hypericin and polylysine (FIG. 2B). As the molar ratio of hypericin:polylysine increases, the ratio of absorption at 605 nm:550 nm increases, indicating formation of the complex.

The ability of hypericin-polylysine complexes to further bind DNA was examined by mixing a 36-nucleotide DNA end-labeled with $^{32}P$ with the hypericin-polylysine mixture. The final mixture was then subjected to electrophoresis in an SDS-polyacrylamide gel. In this gel system, large complexes do not enter the gel and remain at the application site at the top of the gel. In the samples containing DNA alone or DNA and hypericin without polylysine, the radiolabelled DNA entered the gel unhindered and migrated to the bottom of the gel. By contrast, in the sample containing DNA, hypericin, and polylysine, the radioactivity did not enter the gel but remained concentrated at the top of the gel. This provided direct evidence for complex formation between DNA, hypericin and polylysine.

EXAMPLE 2

Association of DNA with Murine T-lymphoblastoid Cells Using a DNA-polylysine-hypericin Complex In the experiments described below, the RL-12 murine lymphoblastoid cell line was used (Bach et al., 1984, *J. Exp. Med.*, 160:270). The cells were maintained in suspension culture in RPMI-1640 supplemented with 10% fetal bovine serum at 37° C. in a humidified atmosphere of 5% $CO_2$. For use in the experiment, cells were suspended at a concentration of $2 \times 10^5$ cells/ml in growth medium, and 2 ml of cells were used for each sample.

For preparation of DNA complexes, polylysine and hypericin were first mixed in different molar ratios as outlined in protocols A–C below. High molecular weight polylysine (Sigma P-1886, molecular weight=350,000, degree of polymerization=1600) was used in Protocol A, while low-molecular weight polylysine (Sigma, Catalog No. P-6516, molecular weight=7–8,000, degree of polymerization=60–80) was used in Protocols B and C.

Hypericin was synthesized from emodin as described (Brockmann et al., 1958, *Chem. Ber.*, 90:2302). A solution of 2 mg/ml in ethanol was prepared by sonication, which was used as outlined below.

| PROTOCOL A HYPERICIN + HIGH MOLECULAR WEIGHT POLYLYSINE | | | |
|---|---|---|---|
| Sample | HY (μl) | PL (1 mg/ml) | $H_2O$ |
| 1 PL only | — | 175 μl | |
| 2 HY:PL 10:1 | 1.25 | 175 μl | — |
| 3 HY:PL 30:1 | 3.75 | 175 μl | — |
| 4 HY:PL 100:1 | 12.5 | 175 μl | — |
| 5 HY:PL 250:1 | 31.5 | 175 μl | — |

-continued

| | | | |
|---|---|---|---|
| 6 HY only (30 μM) | 1.25 | — | 175 μl |
| 7 HY only (100 μM) | 3.75 | — | 175 μl |
| 8 HY only (300 μM) | 12.5 | — | 175 μl |
| 9 HY only (750 μM) | 31.75 | — | 175 μl |
| 10 DNA only | — | — | 175 μl |

PROTOCOL B
HYPERICIN + LOW MOLECULAR WEIGHT POLYLYSINE

| Sample | HY (μl) | PL (0.2 mg/ml) | Buffer |
|---|---|---|---|
| 1 PL only | — | 200 μl | 15 μl |
| 2 HY:PL 1:1 | 1.25 | 200 μl | 15 μl |
| 3 HY:PL 4:1 | 6.0 | 200 μl | 15 μl |
| 4 HY:PL 10:1 | 12.5 | 200 μl | 15 μl |
| 5 HY:PL 20:1 | 25.0 | 200 μl | 15 μl |
| 6 DNA only | — | 200 μl $H_2O$ | 15 μl |
| 7 HY only | 6.0 | 200 μl $H_2O$ | 15 μl |
| 8 HY only | 25.0 | 175 μl $H_2O$ | 15 μl |

PROTOCOL C
HYPERICIN ANALOGUES + LOW MOLECULAR WEIGHT POLYLYSINE

| Sample | HY analogue (μl) | PL (0.2 mg/ml) | $H_2O$ |
|---|---|---|---|
| 1 DNA only | — | — | 200 μl |
| 2 PL only | — | 200 μl | — |
| 3 HY:PL 1:1 | 1.25 μl | 200 μl | — |
| 4 HY:PL 10:1 | 12.5 μl | 200 μl | — |
| 5 HY:Me Ester:PL 1:1 | 1.5 μl | 200 μl | — |
| 6 HY:Me Ester:PL 10:1 | 1.5 μl | 200 μl | — |
| 7 Des-Me HY:PL 1:1 | 1.2 μl | 200 μl | — |
| 8 Des-Me HY:PL 10:1 | 1.2 μl | 200 μl | — |

The hypericin-polylysine mixtures were either used undiluted, or were diluted in water before addition of DNA as indicated in Tables 1–3. The DNA was a 36-nucleotide single-stranded molecule, having the sequence 5'-CCAGGCTGTTCCGCAGATTGTGCGGCGCCCCTG ACT -3' SEQ. ID. NO.:1, which had been labelled with $^{32}P$ using polynucleotide kinase (Stratagene). The specific radio-activity of the DNA was $1.85 \times 10^5$ cpm/μg.

In the experiment shown in Protocol A, the cells were washed once with phosphate-buffered saline, resuspended at a concentration of $4 \times 10^5$ cells/ml in growth medium, and distributed in 2-ml aliquots into 10-ml polypropylene tubes (Falcon). 55 μl of the hypericin-polylysine-DNA mixtures were then added to the cells in duplicate, and mixed. The cells were then incubated at 37° C. for 30 min or 5 hours. In the experiments shown in Protocols B and C, the cells were resuspended at a concentration of $7.5 \times 10^5$ cells/ml, 40 μl of hypericin-polylysine-DNA were added, and the cells were incubated for 4 hours.

Following incubation of cells with the DNA mixtures, the cells were harvested on GF/C filters (Millipore), and washed five times with phosphate-buffered saline. The total amount of radiolabelled DNA bound to the cells was then determined by scintillation counting.

The results of these experiments are shown in Tables 1–3, corresponding to Protocols A–C, respectively.

TABLE 1

CELL ASSOCIATION OF DNA-HYPERICIN-POLYLYSINE COMPLEXES (CPM)

| | TIME OF INCUBATION | |
|---|---|---|
| SAMPLE | 0.5 hrs. | 5 hrs. |
| 1 Polylysine only | 6,170 | 8,628 |
| 2 HY + Polylys 10:1 | 7,924 | 8,634 |
| 3 HY + Polylys 30:1 | 6,996 | 9,012 |
| 4 HY + Polylys 100:1 | 11,906 | 12,504 |
| 5 HY + Polylys 250:1 | 16,432 | 21,448 |
| 6 HY 30 μM only | 778 | 366 |
| 7 HY 100 μM only | 2,048 | 618 |
| 8 HY 300 μM only | 4,018 | 508 |
| 9 HY 750 μM only | 3,222 | 212 |
| 10 DNA Control | 128 | 82 |

TABLE 2

BINDING OF $^{32}P$-DNA TO CELLS

| | HY-polylys. 1:1 & 2 μl DNA | HY-polylys. 1:4 & 2 μl DNA |
|---|---|---|
| 1 control | 14,208/14,218 | 13,912/14,480 |
| 2 1:1 | 49,886/50,254 | 40,030/41,054 |
| 3 4:1 | 37,692/37,636 | 38,938/41,724 |
| 4 10:1 | 19,930/19,286 | 33,364/34,636 |
| 5 20:1 | 9,106/8,998 | 7,704/8,072 |
| 6 DNA control | 1,002/864 | 1,038/1,074 |
| 7 HY equiv. to #3 | 2,746/2,980 | 3,816/9,066 |
| 8 HY equiv. to #5 | 2,222/2,554 | 7,804/5,792 |
| Total DNA in sample | 114,260 | 82,484 |

TABLE 3

| | Hy-polylys. 1:1 & 3 μl DNA | Hy-polylys. 1:8 & 3 μl DNA | Percent of DNA bound to cells from total DNA. Data from: Dilution of hypericin:polylysine | |
|---|---|---|---|---|
| | | | 1:1 | 1:8 |
| 1 DNA alone no carrier | 2,060/956 | 2,060/956 | 1.05% | 1.05% |
| 2 Polylysine control | 6,594/8,568 | 4,295/6,649 | 5.31% | 3.77% |
| 3 HY:Polylysine 1:1 ratio | 90,216/90,716 | 68,725/71,095 | 63.47% | 49.05% |
| 4 HY:Polylysine 10:1 ratio | 105,840/110,817 | 78,773/80,710 | 75.88% | 55.93% |
| 5 HY-Me Ester:Polys. 1:1 ratio | 56,359/56,056 | 26,977/29,806 | 39.43% | 19.92% |
| 6 HY-Me Ester:Polys. 10:1 ratio | 85,902/82,855 | 56,918/58,465 | 59.20% | 40.48% |
| 7 Des-Me HY:Polys. 1:1 ratio | 62,244/58,670 | 19,161/21,709 | 42.42% | 14.33% |
| 8 Des-Me HY:Polys. 10:1 ratio | 78,278/82,568 | 57,080/56,711 | 56.43% | 39.92% |

Table 1 shows that the use of hypericin in conjunction with high-molecular-weight polylysine enhanced the level of cell-associated DNA over that seen with DNA alone, hypericin alone, or polylysine alone. When hypericin was used in conjunction with low-molecular weight polylysine, 40–50% of the DNA became cell-associated versus approximately 1% when the DNA was added to the cells in the absence of hypericin or polylysine. Table 3 shows that the hypericin analogues hypericin methyl ester and desmethyl hypericin were also effective at enhancing the uptake of DNA into lymphoblastoid cells.

EXAMPLE 3

Inhibition of HIV p55 Gag Expression by Delivery of Gag Antisense Oligonucleotides in a Complex with Hypericin and Polylysine In this experiment, CEM cells infected by HIV were used as targets to test the uptake and activity of DNA complexed with hypericin and polylysine. The rationale of this experiment was that uptake of HIV gag-specific antisense DNA would result in decreased expression of the p55 protein which is encoded by this gag region. Therefore, expression of p55 was assayed at two and three weeks following exposure of the cells to gag-specific antisense DNA or control DNA.

CEM cells were maintained in culture in RPMI-1640 supplemented with 10% fetal bovine serum and antibiotics. Cells at a concentration of $5-10\times10^5$ cells/ml were infected with HIV by adding $10^3$ tissue culture infectious doses ($TCID_{50}$) of HIV in the presence of 2 µg/ml polybrene.

The DNA used was either an antisense phosphorothioate oligonucleotide having the sequence 5'-CGCTCTCGCACCCATCTCTCTCCTTCTA-3', SEQ. ID. NO.:2. corresponding to the sequence complement of nucleotides 776–802 of the HIV gag gene (Lisziewicz et al., 1993, Proc. Natl. Acad. Sci. USA, 90:3860–3864), or a control "random" phosphorothioate oligonucleotide (hereinafter referred to as RnDom DNA) of identical length. The DNAs were synthesized on an automated synthesizer (Biosearch 8750, Millipore) as described (Agrawal et al., 1989, Proc. Natl. Acad. Sci. USA, 86:7790–7794.) Each DNA sample was used to prepare three stock solutions, of 1 mg/ml, 0.1 mg/ml, and 0.01 mg/ml.

Low-molecular weight polylysine (Sigma P-6516, molecular weight=7–8,000) was prepared as a 0.1 mg/ml solution. Hypericin was prepared as a 2 mg/ml solution in ethanol. Addition of 3 µl hypericin to 800 µl polylysine resulted in a 1:1 molar ratio of the two compounds. This solution was either used as is, or was diluted 1:5 before addition of DNA. Similarly, the polylysine stock and the hypericin stock were also used undiluted, or were diluted 1:5 to provide control solutions. These solutions were designated HY-polylys 1 and 1/5; Polylys 1 and 1/5; and HY 1 and 1/5, respectively.

51.5 µl of the polylysine, hypericin, and polylysine-hypericin solutions described above were then mixed with 4.5 µl of solutions of antisense or control DNA to result in three different concentrations of DNA for each solution: 300 µg/100 µl; 30 µg/100 µl; and 3 µg/100 µl. These were designated DNA 300, 30, and 3; and RnDom DNA 300, 30 and 3, respectively. 5 µl of a 10-fold concentrated buffer were then added, and the mixtures were incubated for 15 minutes at 40° C. Then, 6 µl of each solution was added to 150 µl CEM cultures, and the cultures were shaken. The DNA administration was repeated every 3 days.

At two and three weeks following initial exposure to DNA, HIV p55 was measured, using an ELISA assay. Briefly, a rabbit anti-p55 antibody is bound to a microtiter plate. Cell lysates were incubated with the plates, allowing p55 to bind. A second, biotinylated anti-p55 antibody is then added, followed by streptavidin conjugated to peroxidase.

Figure 3:
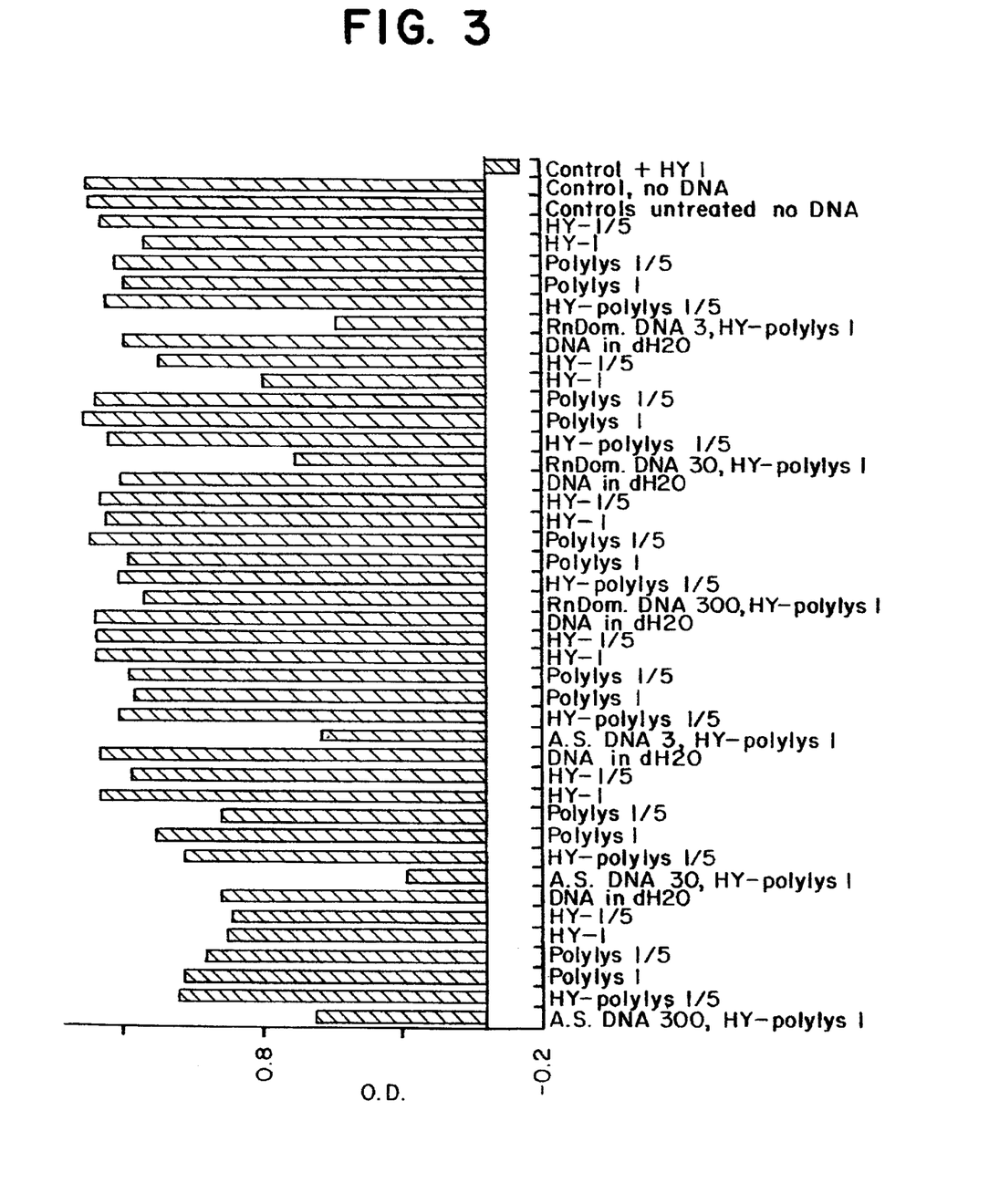
FIG. 3 shows the expression of HIV p55 gag protein in HIV-infected CEM cells 14 days after exposure of the cells to a p55 antisense oligonucleotide or to a random oligonucleotide, with and without hypericin alone, polylysine alone, or hypericin-polylysine.
Figure 4:
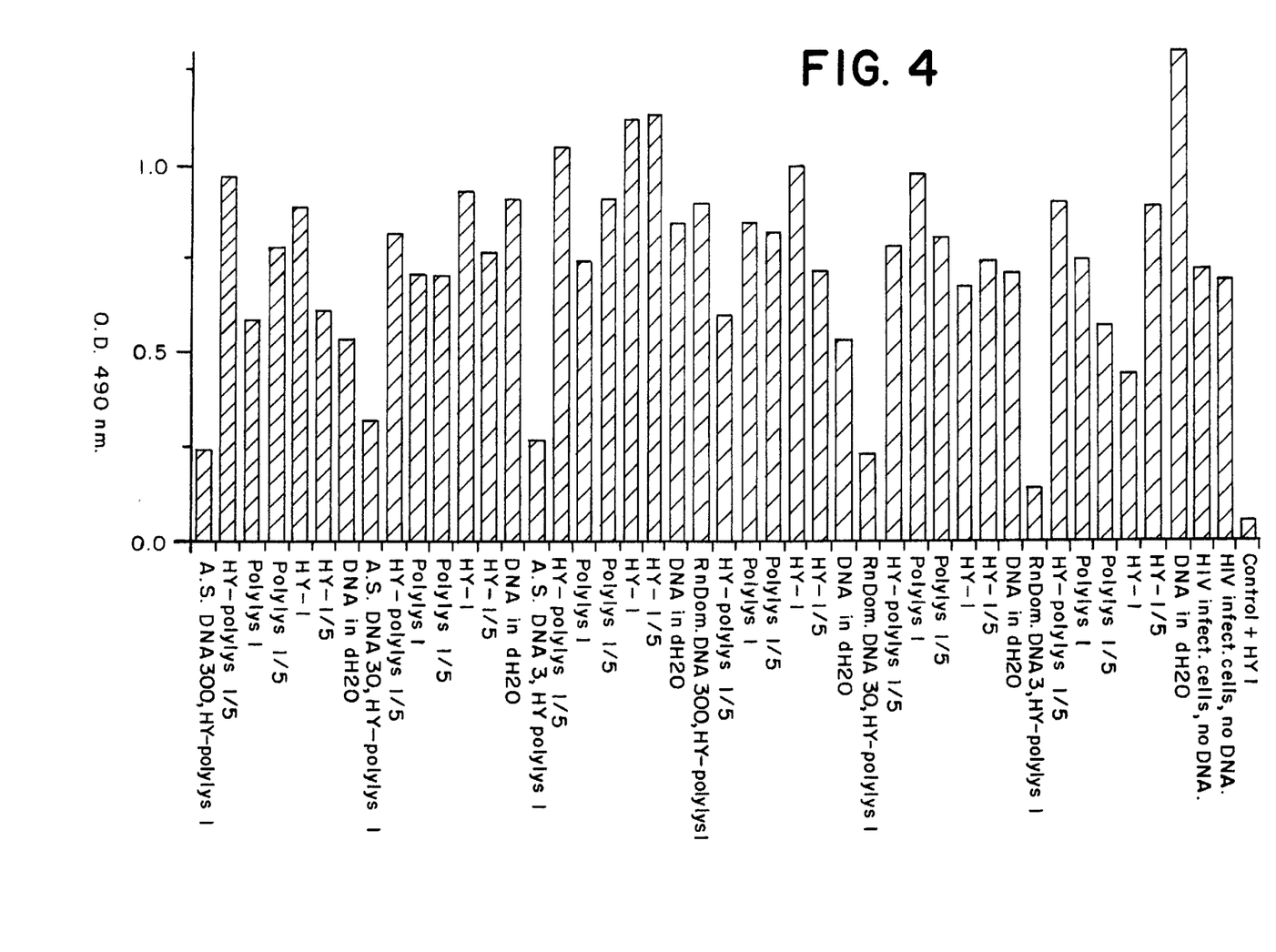
FIG. 4 shows the expression of HIV p55 gag protein in HIV-infected CEM cells 21 days after exposure of the cells to a p55 antisense oligonucleotide or to a random oligonucleotide, with and without hypericin alone, polylysine alone, or hypericin-polylysine.

The results are shown in FIGS. 3 and 4. It is evident that the most effective inhibition of p55 expression occurred in cultures exposed to DNA complexed with hypericin and polylysine, and that DNA alone, hypericin alone, and polylysine alone were relatively ineffective. These data support the application of the methods of the present invention in delivering nucleic acids to cells.

---

What is claimed is:

1. A method for delivering nucleic acids to cells comprising the steps of:
   (i) contacting
      (a) hypericin or a hypericin analogue, or salts thereof; and
      (b) a polycation to form a non-covalent binary complex;
   (ii) incubating said binary complex with said nucleic acid, wherein said incubating step forms a non-covalent ternary complex between said hypericin or hypericin analogue, said polycation, and said nucleic acid; and
   (iii) contacting said cells with said ternary complex.

2. The method of claim 1, wherein said salt comprises sodium or potassium.

3. The method of claim 1, wherein said nucleic acid comprises linear or circular deoxyribonucleic acid (DNA).

4. The method of claim 3, wherein said DNA comprises antisense oligonucleotides.

5. The method of claim 4, wherein said DNA comprises phosphorothioate oligonucleotides.

6. The method of claim 3, wherein said DNA comprises one or more genes capable of expression within said cells.

7. The method of claim 1, wherein said nucleic acid comprises ribonucleic acid (RNA).

8. The method of claim 7, wherein said RNA is selected from the group consisting of messenger RNA, ribosomal RNA, transfer RNA, 5S RNA, and ribozymes.

9. The method of claim 1, wherein said hypericin or hypericin analogue is selected from the group consisting of hypericin, pseudohypericin, hypericin-methyl ester, hypericin-propyl ester, hypericin isopropyl ester, hypericin-butyl ester, hypericin-isobutyl ester, hypericin dicarboxylic acid, desmethyl hypericin, and hydroxydesmethyl hypericin, and salts thereof.

10. The method of claim 1, wherein said polycation is selected from the group consisting of polylysine, polyarginine, polyasparagine, polymethyleneamine, polyethyleneamine, polypropyleneamine, polyisopropyleneamine, polybutyleneamine, polyisobutyleneamine, polypentyleneamine and polyisopentyleneamine.

11. The method of claim 10, wherein said polycation is polylysine.

12. The method of claim 11, wherein said polylysine comprises polymers of between about 5 and about 10,000 monomers.

13. The method of claim 1, wherein said hypericin or hypericin analogue and said polycation are present in molar ratios from about 1:1 to about 100:1.

14. A method for delivering nucleic acids to cells comprising the steps of:
   (i) contacting hypericin and polylysine to form a non-covalent binary complex;
   (ii) incubating said binary complex with said nucleic acid, wherein said incubating step forms a non-covalent ternary complex between said hypericin, said polycation, and said nucleic acid; and
   (iii) contacting said cells with said ternary complex.

15. A method for delivering nucleic acids to cells expressing cell surface receptors for low-density lipoprotein, comprising the steps of:
   (i) contacting
      (a) hypericin or a hypericin analogue, or salts thereof; and
      (b) a polycation to form a binary complex;
   (ii) incubating said binary complex with said nucleic acid, to form a ternary complex between said hypericin or hypericin analogue, said polycation, and said nucleic acid;
   (iii) incubating said ternary complex with low-density lipoprotein to form a quaternary complex between said hypericin or hypericin analogue, said polycation, said nucleic acid, and said low-density lipoprotein; and
   (iv) contacting said cells with said quaternary complex.

16. A composition comprising:
   (i) hypericin or a hypericin analogue selected from the group consisting of pseudohypericin, hypericin-methyl ester, hypericin-propyl ester, hypericin isopropyl ester, hypericin-butyl ester, hypericin-isobutyl ester, hypericin dicarboxylic acid, desmethyl hypericin, and hydroxydesmethyl hypericin, and salts thereof;
   (ii) a polycation selected from the group consisting of polylysine, polyarginine, polyasparagine, polymethyleneamine, polyethyleneamine, polypropyleneamine, polyisopropyleneamine, polybutyleneamine, polyisobutyleneamine, polypentyleneamine and polyisopentyleneamine; and
   (iii) a nucleic acid selected from the group consisting of linear or circular deoxyribonucleic acid (DNA), ribonucleic acid (RNA), and protein-nucleic acid (PNA).

17. The composition of claim 16, wherein said polycation comprises polylysine and said nucleic acid comprises DNA.

18. A formulation for delivering nucleic acids to cells, comprising:
  (i) the composition according to claim 16; and
  (ii) a physiologically acceptable carrier or diluent.

19. The formulation of claim 18, wherein said polycation comprises polylysine, and said nucleic acid comprises DNA.

* * * * *